(12) United States Patent
Gaál et al.

(10) Patent No.: US 8,226,968 B2
(45) Date of Patent: Jul. 24, 2012

(54) LIPOSOME COMPOSITION

(75) Inventors: József Gaál, Budapest (HU); Laszlone Kollárik, Budapest (HU); András Szego, Budapest (HU)

(73) Assignee: Invencio-21 Gyogyhatasu Keszimenyeket Gyarto KFT, Budapest (HU)

( * ) Notice: Subject to any disclaimer, the term of this patent is extended or adjusted under 35 U.S.C. 154(b) by 228 days.

(21) Appl. No.: 12/665,638

(22) PCT Filed: Jun. 19, 2008

(86) PCT No.: PCT/HU2008/000072
§ 371 (c)(1),
(2), (4) Date: Dec. 18, 2009

(87) PCT Pub. No.: WO2008/155592
PCT Pub. Date: Dec. 24, 2008

(65) Prior Publication Data
US 2010/0178329 A1    Jul. 15, 2010

(30) Foreign Application Priority Data
Jun. 19, 2007  (HU) .................................... 0700426

(51) Int. Cl.
*A01N 25/26* (2006.01)
*A01N 36/00* (2006.01)
(52) U.S. Cl. .................. 424/417; 424/420; 424/725
(58) Field of Classification Search .............. None
See application file for complete search history.

(56) References Cited

U.S. PATENT DOCUMENTS

| 4,544,656 A | * | 10/1985 | O'Sullivan | 514/238.8 |
| 4,784,842 A | * | 11/1988 | London et al. | 424/45 |
| 5,128,139 A | | 7/1992 | Brown et al. | |
| 5,595,756 A | * | 1/1997 | Bally et al. | 424/450 |
| 5,750,108 A | * | 5/1998 | Edwards | 424/727 |
| 6,383,499 B1 | * | 5/2002 | Lipi | 424/523 |

FOREIGN PATENT DOCUMENTS

| DE | 198 00 982 A1 | 7/1999 |
| DE | 198 00 982 A1 * | 7/1999 |
| DE | 199 22 193 A1 | 11/2000 |
| FR | 2 894 483 A1 | 6/2007 |
| JP | 2004-131432 A | 4/2004 |
| WO | 01/66079 A1 * | 9/2001 |

OTHER PUBLICATIONS

Dass etal. Malignant Melanoma of the Mucous Membranes of the Head and Neck: Three Case Reports; Ear, Nose and Thorat, Apr. 2006; 85, 4, p. 268-270.*

(Continued)

*Primary Examiner* — Patricia Leith
(74) *Attorney, Agent, or Firm* — Birch, Stewart, Kolasch & Birch, LLP

(57) ABSTRACT

The invention relates to a liposomal composition, containing a citrus type (Aurantioideae) essential oil of pharmaceutical grade 0.5-5.0 part by weight; lavender oil of pharmaceutical grade 0.5-5.0 part by weight; vitamin E 0.1-1.5 part by weight; vitamin A 0.1-1.5 part by weight; castor oil ethoxylated 1.0-6.0 part by weight; a phospholipid 0.1-1.0 part by weight; distilled water 15-30 part by weight; ethanol 96% 65-75 part by weight. The composition can be used for treatment of wounded, burned, frozen, infected skin surfaces.

19 Claims, 4 Drawing Sheets

OTHER PUBLICATIONS

Partial Translation of Förster, K (DE 198 00 982 A1) by USPTO Translator, copied from email on Sep. 19, 2011, 2 pages.*

Wilson; Beauty Spot; Sunday Mail, Glasgow (UK): Apr. 18, 2004, p. 7 (pp. 1-2 of ProQuestdatabase print-out).*

Zhao, Discovery and Development of Novel Therapeutic Agents for Advanced Melanoma; The University of Tennessee Health Science Center, 2010, 170 pages, Abstractonly provided.*

Olionatura online; Lipodermin; URL< http://www.olionatura.de/_rohstoffe/index.php?id=11> pp. 1-4, accessed Sep. 19, 2011).*

* cited by examiner

LIPOSOME COMPOSITION

The present invention relates to a liposome composition containing essential oils and vitamins.

It is known that the use of medicines and curative compositions either of natural origin or prepared synthetically has been debated since the 19$^{th}$ century. In spite of the debates it is a fact that the pharmacopoeias of developed countries contain several registered compositions having active ingredient of plant origin. By our time the debates made physicians accept such facts that compositions of natural, first of all of plant origin are put on the market with increasing weight.

The use of compositions produced from materials of natural origin is of the same age as the history of mankind.

Many of the materials that can be found in the parts of plants can only be taken into consideration as an active ingredient, when they are used in a concentrated state. In this sense the proteins, carbohydrates, vegetable fats, vitamins existing in the plants in themselves cannot be considered as active ingredients.

An essential aspect of the selection of the effective substance is whether the effective substance is a homogenous compound or a combination of several similar compounds or a mixture of extracts of many different drugs (compounds).

The order of importance of the aspects of the selection is determined by the therapeutic value, the technological possibilities, and economic considerations.

The extraction technologies of effective plant substances are based on physical operations. In some special cases the valuable materials are extracted by a chemical process from the concentrates obtained by physical processes, followed by further physical separation manipulations. After harvesting the medicinal plant and removing the parts of the plant containing no curative substances, drying, cutting, grinding or pressing processes are applied.

The pressing process is suggested for the extraction of the oily (lipophilic) phase from the suitable plant parts.

By extraction carried out with water, alcohol or seldom with oil, the substances of hydrophilic and hydrophobic (lipophilic) character are separated.

The substance obtained by extraction operations (extract) is concentrated and/or purified by further physical methods or a combination thereof. In most cases these include evaporation, distillation or steam distillation.

By addition of alcohol to the aqueous extract the substances which are not soluble in alcohol can be precipitated.

By evaporation of the alcoholic extract tinctures, oils can be obtained. The oils can be distilled in order to reach further purification or separation (fractionation).

The steam distillation is a special process by which the most valuable components of vegetable oils; the oil-soluble compounds can be separated. By this process up to 30-50% of the effective substances can be extracted.

The essential oils or their concentrates are the chemically, pharmaceutically, technologically best known active substances of plant origin.

They got their collective name after their property that they evaporate without leaving any residue. They are intensively evaporating materials having a strong fragrance.

Almost all of them can be mixed freely with each other. Nearly all of them can be freely diluted with fats, vegetable oils.

The essential oils can be isolated from the suitably selected plant part by steam distillation, cold pressing, alcoholic extraction (ca. 75% by steam distillation, 20% alcoholic extract, 5% cold pressed oil).

There are about 100 types of essential oils on the market, of which about 50 types are applied in aroma therapy, scent therapy. 10-20 types of oils are registered products in national pharmacopoeias for human medication. (In some Far East pharmacopoeias more than 20 active substances are registered.) They exert their physiological effect in 2-50 mg single, 10-500 mg daily doses. Depending on geographical conditions and cultures they are frequently used for personal hygiene and in beauty preparations.

We compared the therapeutic effect of 14 essential oils on human skin (in the case of 8 indications: inflammation, regeneration, eczema, hair falling, foot mycosis, pregnancy lines (stretch marks), cellulitis, herpes). The results are summarized in Table 1

| Essential oil | Effect on skin alone | Effect on skin in mixture | General inflammation reducing effect | Skin-inflammation inhibiting effect | Skin-regenerating effect |
|---|---|---|---|---|---|
| 1. Bergamot | 1 | 0 | + | − | − |
| 2. Juniper | 3 | 1 | − | + | − |
| 3. Cedar | 2 | 0 | − | + | − |
| 4. Cypress | 2 | 0 | − | − | − |
| 5. Lemon | 2 | 3 | + | + | + |
| 6. Geranium | 3 | 3 | − | + | − |
| 7. Lavender | 7 | 1 | + | + | + |
| 8. Myrrh | 2 | 2 | + | − | + |
| 9. Rosemary | 1 | 1 | + | − | − |
| 10. Rose | 1 | 1 | + | − | − |
| 11. Rose-tree | 0 | 2 | − | + | − |
| 12. Sandal | 2 | 1 | + | + | − |
| 13. Tea tree | 2 | 0 | + | − | − |
| 14. Incense | 1 | 1 | + | − | + |

Meaning of the Expressions Used in Table 1

"Effect on skin alone" means the number of indications out of the 8 indication in which the given essential oil has an effect in itself "Effect on skin in mixture" means the number of further indications out of the 8 indications in which the given essential oil has an effect in combination with other essential oil "General inflammation reducing effect"
+: the given essential oil has a reducing effect
−: the given essential oil is ineffective "Skin-inflammation inhibiting effect"
+: the given essential oil has an inhibiting effect
−: the given essential oil is ineffective "Skin-regenerating effect"
+: effective
−: ineffective.

Table 1 shows that the lemon oil and the lavender oil have the most versatile therapeutic effects on skin.

The lavender oil can be obtained from the fresh flowering top part of the *Lavandula angustifolia* by steam distillation, followed by suitable refining. The essential oil content of the plant is 1%.

Pharmacopoeia quality: Lavandulae Aetheroleum
Identified components according to the Ph. Eu. 4.1:
linalyl acetate 25-46%; linalol 20-45%; terpinen-4-ol max. 6%; as well as limonene, cineol, camphor, lavandulyl acetate, levandulol, α-terpineol, 3-octanone components from several thousandth up to max. 2.5%.

According to Ph. Hg. VII it should contain linalol and its acetic acid ester in 35-60%.

In the Pharmacopoeias several physical parameters are given for the oils which can be used (density, refraction index, optical rotation etc.).

In aroma therapy the lavender oil is a universal essential oil used in the widest field of indications, applied from the earliest times.

It is used for the treatment of
any wound, especially which is slow in healing, inflamed, festering,
burned, ulcerous, eczemic skin surface, and
sunburned skin.

In special pharmacopoeias the allowed daily therapeutic dose is 70-300 mg.

The lemon oil is squeezed cold from the peel of the fresh fruit of *Citrus medica* L. ssp. *limonon*.

This part of the plant contains 1.5% essential oil.
Identified components according to Ph. Eu.4.1:
limonene 56-78%, β-pyrene 7-17%, γ-terpinene 6-12%, nerale, nerale acetate, (citrale B) 0.3-1.5%, geranal, geranal acetate 1-2.3% (citral A), sabinen, β-cariofeil max: 3%.

According to Ph. Hg. VII the citral content is to be 3-6%.

As in the case of lavender oil, the Pharmacopoeias subject the use of the lemon oil to physical parameters. The use of lemon oil in aroma therapy has two special properties. This is the only oil type among the oils used all over the world, which is obtained by cold squeezing (without the aid of heat) from six citrus family [lemon (*Citrus limonum*), orange (*Citrus aurantium eulcia*), mandarin (*Citrus madiurensis*), grapefruit or pampelmusse (*Citrus maxima*), limett (*Citrus aurantifolia* Swingle), bergamot (*Citrus aurantium*). In the essential oil squeezed from the fresh peel of the fruits belonging to this plant family the same chemical materials can be found and roughly in the same ratio. In aroma therapy the use of lemon oil was suggested for many indications. Excellent activities are declared as for the skin, bacteria, fungi and viruses. These properties were described also for the vapors of the essential oil.

According to one description 210 bacterium culture including 12 mould fungi and staphylococcus culture were subjected to the vapor of the essential oil, and after 15 minutes only 14, after half an hour only 4 bacterium cultures were alive. All of the mould fungi and the staphylococcus culture were destroyed.

According to another description the essential oil vapors destroyed the meningococcus in 15 minutes, the pathogen of typhus in 1 hour, the pneumococcus in 2-3 hours, the streptococcus nemlyticus in 3-12 hours.

Through direct contact the essential oil destroyed the staphylococcus and the pathogen of typhus in 5 minutes, the pathogen of diphtheria in 20 minutes.

French Sources (Griffoln, Rochix and Morel)

As in the case of lavender oil wound healing, antiinflammatory, haemostatic, festeric wound healing effects, and application for treatment of frostbite were described. In pharmacopoeias 60-120 mg daily therapeutic doses are allowed.

The biological activity of the vitamins is known. Primarily in small doses they have physiological role in prevention of pathological processes, as well as in the acceleration of health restoration and rehabilitation.

Thus, the vitamin A
increases the resistance of the skin and mucous membrane,
accelerates the healing of ulcerous wound,
regulates the function of sebaceous glands,
protects the epithelium and increases its resistance against infections.

The vitamin E
increases the effect of vitamin "A",
inhibits the rough cicatrisation,
accelerates the healing of burn,
has vasodilative, anticoagulant effect and
is an antioxidant.

The lecithins (phosphatidyl choline, choline phosphoglyceride) are important components of the organic building blocks of the living world.

The basic elements of the lecithins are the glycerol, phosphoric acid and fatty acid molecules. Because of the variability of the fatty acid groups great number of compounds can be synthesized.

In the living world soy and eggs contain lecithin in the highest quantity.

The lecithin molecule has hydrophilic character because of the structure of the phosphoric acid group (in form of free acid or salt), and lipophilic character due to the presence of the fatty acid (lipid). This dual feature ensures the significant physical, chemical and biological effects. The lecithin molecules create well-arranged structure (micelles) in themselves (reduction of interfacial tension) and by connecting to each other. In the formation of this well-arranged structure the hydrophilic-lipophilic character of the medium surrounding the lecithin has an important role. The shape and size of these well-arranged structures depend on the chemical structure of the lecithin and the medium in which it forms. According to the most ingenious analogy "the lecithins are the tensides of the living world".

From the micelles by the formation of a closed structure a liposome can be created. Similarly to the synthetic tensides the well-arranged structures are able to enclose foreign materials. This often means not only a physical arrangement but also the establishment of a bound between the lecithin and the foreign material, where the degree and type of the bound are in connection with the chemical, superficial, physico-chemical properties of the foreign material. The arrangement of the lecithin in the plane is laminar, but in the further spatial arrangement the lecithin can create many geometrical forms.

The simplest structure is a laminar structure. These structures can create one layer or more layers depending on how well it is arranged.

These are the so-called
small unilamellar vesicles (SUV)
large unilamellar vesicles (LUV)
multilamellar multilayer (MLV) liposomes.

In preparation of such liposomes we can exploit that under suitable conditions (depending on structure, pH, temperature and the polarity of the medium) the lipids get into transitional liquid-crystalline state. By reaching this transitional state a liposome can be created. The aim of the methods of preparation is also to reach this transitional state. Accordingly, the process of including the "foreign material" into the lecithin liposome is complex and depends on many parameters.

Typical processes for the preparation of liposomes:
dissolution of components into a solvent, the evaporation of the solvent, then liposome formation by hydratation, changing the polarity of the solvent,
treatment with ultrasound (half-mechanical),
emulsion technique with changing the polarity of the medium,
dialysis.

The special biological activity of the foreign material enclosed in the liposome is based on the fact that the construction of the organism and the liposome is of a similar structure. This similar structure allows selective "targeting"; a directed forwarding to the target.

The foreign material enclosed in the Liposome is able to exert its effect selectively or on a higher level of activity. The utilization of this can open new perspectives for the application of liposomes of materials known per se.

The subject of the present invention is the inclusion of two materials (essential oil, vitamin) defined in a liposome as "foreign materials" into a special liposome structure.

The subject of our invention is particularly a liposome composition, characterized in that it contains the following components:

| | |
|---|---|
| a citrus type (Aurantioideae) essential oil of pharmaceutical grade | 0.5-5.0 part by weight |
| lavender oil of pharmaceutical grade | 0.5-5.0 part by weight |
| vitamin E | 0.1-1.5 part by weight |
| vitamin A | 0.1-1.5 part by weight |
| castor oil ethoxylated | 1.0-6.0 part by weight |
| a phospholipid | 0.1-1.0 part by weight |
| distilled water | 15-30 part by weight |
| ethanol 96% | 65-75 part by weight |

The composition according to the invention contains independently preferably
1.5 part by weight a citrus type essential oil
2.0 part by weight lavender oil
0.5 part by weight vitamin E
0.5 part by weight vitamin A
0.5 part by weight phospholipid
3.5 part by weight castor oil ethoxylated
23 part by weight distilled water
68 part by weight ethanol 96%.

The composition according to the invention contains independently preferably lemon oil as citrus type essential oil, lecithin as phospholipid.

In the composition according to the invention the ethoxylated castor oil contains preferable 30-40 moles, more preferably 35 moles of ethylene oxide.

The composition according to the invention can be prepared in the following way: to the mixture of 0.5-5.0 part by weight of citrus type essential oil, and 0.5-5.0 part by weight of lavender oil the mixture of 0.1-1.0 part by weight of vitamin E and 0.1-1.5 part by weight of vitamin A, then 1.0-6.0 part by weight of ethoxylated castor oil is added, in the oil phase obtained 0.1-1.0 part by weight of phospholipid is dissolved, and
by adding 15-30 part by weight of distilled water of 45° C., a liposomal hydrophilic phase is formed, which is converted into a liposomal lipophilic composition by phase inversion elicited by addition of 65-75 part by weight of 96% ethanol, or
by adding 65-75 part by weight of 96% ethanol a liposomal lipophilic phase is formed, which is converted into liposomal hydrophilic composition by phase inversion elicited by addition of 15-30 part by weight of distilled water of 45° C.

The composition according to the invention is prepared preferably by hydrophilic-lipophilic phase inversion.

The composition according to the invention can be used for the treatment of skin injuries like wound, burned, frozen, or infected skin surfaces more effectively than the compositions available on the market.

Compositions of Example 6 (liposome formulation) and Example 13 (non liposome formulation) and $AgNO_3$ (as reference group) were tested in the case of open wound healing in rat in the following models:
1. Chemically initiated wound (ulcer, acetic acid)
2. Burned wounds
3. Diabetic wound Methods All work (animal housing, experimentation, euthanasia, disposal) was performed substantially in accordance with the International Guiding Principles for Biochemical Research Involving Animals as stipulated by the EU Council (Directive 86/609/EEC).

Chemically Initiated Wound

An experimental skin ulcer was initiated by intradermal injection of acetic acid. Injection of glacial acetic acid to the skin in the left hind leg instep of rats resulted in the necrosis of the skin, and a skin ulcer developed in 3 days. The ulcer area reached its peak (around 15 $mm^2$) on the 5th day, and it was necretomised. It recovered to its control level within 6 weeks.

30 rats were divided into 3 groups. Each group had 10 animals. After chemically induced ulcers of rats according to the above-described procedure, each rat was caged individually.

Group 1
10 rats were treated twice daily with 3.5 mg* of the composition of Example 6

Group 2
10 rats were treated twice daily with 3.5 mg* of the composition of Example 13

Group 3
10 rats were treated with the same amount of 1.5% $AgNO_3$* solution (control)

*The animals were treated by spray with 4 exposition from 5 cm distance. The dose was calculated based on active ingredient delivered to the damaged surface.

From each group on days 7, 14 and 21 one rat was sacrificed for hystopathological examination.

On day 50 the rest of rats from each group were sacrificed. Sacrifice of the rats were done using an overdose of sodium pentobarbital.

During 50 days all animals were evaluated for the following healing parameters: crust formation, inflammation, formation of granulation tissue and re-epithelization.

FIG. 1 shows the recovery after chemically induced wound.

Result:

Both of the treated animal groups produced a significantly faster regeneration compared to control. The liposomal formulation is more effective in the same concentration range.

Burned Wounds

Each animal was anesthetized with sodium pentobarbital administered i/p (5 mg/25 g). The hair over the dorsum was clipped with animal clippers. The animal was placed supine in the burning device. Ten seconds of exposure was sufficient to produce a full-thickness burn. On removal from the water, the dorsum was quickly dried by rolling on a towel and the animal was released and individually caged. This procedure produces a uniform burn about 40 mm² with sharp margins.

30 rats were divided into 3 groups. Each group had 10 animals. After burning rats according to the above-described procedure, each rat was caged individually.

Group 1

10 rats were treated twice daily with 3.5 mg* of the composition of Example 6

Group 2

10 rats were treated twice daily with 3.5 mg* of the composition of Example 13

Group 3

10 rats were treated with the same amount of 1.5% $AgNO_3$* solution (control)

*The animals were treated by spray with 4 exposition from 5 cm distance. The dose was calculated based on active ingredient delivered to the damaged surface the surface.

On days 7, 14, 25 and 50 after the burn was effected animals were sacrificed by overdose of sodium pentobarbital and skin specimens were taken for histopathology and blood for procalcitonin (PCT) and C-reactive protein determination.

The PCT level was determined on a LIAISON automatic chemiluminescent equipment using Brahms PCT immunoassay.

The C-reactive protein was measured according to Hutchinson et al. Clin. Chem. 2000; 46:934-8.

During the microscopic and macroscopic observations, four wound healing parameters were evaluated: crust formation, re-epithelialization, formation of granulation tissue and inflammation.

Results

There were no significant differences in crust formation between groups. But anti-inflammation effect during wound healing was more pronounced in the groups 1 and 2.

Granulation tissue was prominently developed in the groups 1 and 2.

Re-epithelization in the middle part of the burn wounds was faster on all rats of groups 1 and 2 compared with $AgNO_3$ control.

The time frame of wound recovery is summarized in FIG. 2

The procalcitonin and C reactive protein level on the days of hystopathological examination was also measured.

The results of these examinations are summarized in FIG. 3 and FIG. 4

Both the inflammation and the septic parameter labels were better in the treated groups indicating the positive effects of the treatment and the superiority of the liposomal formulation.

Diabetic Wound

Firstly, a diabetic animal model was established by streptozotocin injection. Then standard wounds were created on the feet of the diabetic rats. (Eur Surg Res. 2008 Apr. 2; 41(1):15-23). Subjects used were male Sprague-Dawley rats 5 to 6 weeks old.

The average ulcer area was developed after 10 day of initial treatment about 20 mm² in the all groups. After this period (in the figure 0 time) animals were treated (by spray with 4 exposition from 5 cm distance) of the Composition of Example 6 and Example 13 in sum with 3.5 mg active ingredient. The recovery time was compared. The wound surface was measured in the control group every tenth day and in the treated groups every fifth day.

FIG. 5 shows typical figures of the recovery of the diabetic ulcers

FIG. 6 shows the time frame of the healing of the diabetic wounds

Result:

The regeneration in the treated groups are significantly faster. The liposome formulation, because of better penetration of the active ingredient produces an additive positive effect.

Further details of the invention are given in the examples without limiting the invention to the content thereof.

EXAMPLES

General

Component A (Essential Oil)

1.5 g of lemon oil t=20° C. is mixed with 2 g of lavender oil. Homogenous solution is obtained.

Component B 0.5 g of vitamin A t=20° C. is mixed with 0.5 g vitamin E. Homogenous solution is obtained.

Components C (Co-Solvent)

3.5 g of ethoxylated castor oil is weighed.

Component D (Phospholipid)

0.5 g of soy lecithin is weighed.

Component E (Water)

23 g of distilled water t=45° C. is weighed.

Component F (Alcohol)

68.5 g of 96% ethanol t=20° C. is weighed

Component G (Alcohol)

68.5 g of 96% ethanol t=20° C. is weighed

Component H (Water)

23 g of distilled water t=45° C. is weighed.

Out of the 8 components the given ones are mixed in the way indicated in the Examples 1-12 in Table 2. The mixing of the components is carried out in alphabetical order. The composition and the way of preparation of the Example 13 is identical with those of Example 6 except that the temperature of water used as Component E is t=20° C.

In Examples 1-6 after the different mixing of the components (A, B, C, D) by contacting the mixture with the Component E a hydrophilic phase (aqueous phase) is obtained, then by contacting it with the Component G, due to phase inversion a lipophilic phase is obtained.

The first series of evaluation is a subjective one made by means of microscope. By using nanolaser particle size analyser the size distribution by weight is measured.

In Examples 7-12 the way of mixing the A, B, C, D components is identical with that of Examples 1-6 with the exception that the further contacting is carried out with "Component F", and thus lipid (alcoholic) phases are formed. These lipid phases are contacted with the (aqueous) Component H in order to cause phase inversion, and thus hydrophilic phases are formed. The second evaluation series is also carried out by means of microscope and particle size analyser.

Evaluation:

The important measurement parameters of the evaluations are summarized in Table 3 and Table 4.

Instruments:

1. Laser particle size analyser of Malvern Mastersizer 2000 type.

Measuring range: 0.02-2000 [μm].

The instrument measures the weight distribution of our disperse system in function of particle size.

2. Carl Zeiss polarization microscope.

The meaning of signs used in the Table:

UN=the sign of disperse system sample not subjected to ultrasonic treatment

UN1=the sign of sample subjected to ultrasonic treatment for 1 minute

UN2=the sign of sample subjected to ultrasonic treatment for 2 minutes d=the average size of particle size measured in function of weight in [μm]

dmax (d1, d2, d3, . . . dn)=the size of the maximum of differential distribution corresponding to d1, d2, d3, . . . dn components in [μm]

V % (V1, V2, . . . Vn)=volume % belonging to dmax (d1, d2, d3, . . . dn)

VNd (10, 50, 90) %=the particle size in [μm] corresponding to 10, 50 and 90% by volume in a sample not subjected to ultrasonic treatment.

Example 1

The sample containing essential oil and co-solvent forms unstable emulsion of heterogenous phase in water (Component E). In the rough dispersion there are components of 4 different size distribution, which after addition of alcohol (Component G) dissolve.

Example 2

In the essential oil component the phospholipid (Component D) does not dissolve even in the presence of co-solvent.

Example 3

The solution containing vitamin and co-solvent forms with water (Component E) a finer heterodisperse spontaneous emulsion than the essential oil, which gets even finer under ultrasonic treatment. The average drop size of the emulsion decreases (from 27.6 [μm] to 11.2 [μm]) after the addition of alcohol (Component G). The ultrasonic treatment further increases the dispersion degree (the drop size decreases from 11.2 [μm] to 6.5 [μm]).

Example 4

The phase containing vitamin and co-solvent cannot dissolve the phospholipid (D) component.

Example 5

The vitamin, the essential oil, and the co-solvent solution forms fine emulsion, which becomes rougher under ultrasonic treatment. The alcoholic phase inversion further decreases the drop size of the emulsion (from 3.6 [μm] to 1.3 [μm]). The sample not subjected to ultrasonic treatment forms a stable microemulsion.

Example 6

When phospholipid is added to the hydrophilic phase containing essential oil, vitamin and co-solvent, a solution forms.

After contacting this solution with water a rough, multilaminar liposome of heterogeneous phase is formed. This rough dispersion can be converted into a finer homodisperse large multilaminar liposome by ultrasonic treatment (the size decreases from 478 [μm] to 50.1 [μm]). By alcoholic phase inversion a multilaminar liposome of fine distribution is obtained (with an average size of 3.6 [μm]). The ultrasonic treatment elicits a coagulation process which results in growing particle size (it grows from 3.6 [μm] to 7.7 [μm]).

Example 7

The essential oil and the co-solvent dissolves in alcohol. After the phase inversion elicited by water the solution remains clear.

Example 8

The phospholipid does not dissolve in the mixture of essential oil and co-solvent, even if alcohol is added.

Example 9

The mixture of vitamin and co-solvent dissolves in the alcohol. After the phase inversion elicited by water nice homodisperse microemulsion (of 0.6 {μm}) forms, which becomes somewhat rougher (from 0.6 [μm] to 2.9 [μm]) under ultrasonic treatment.

Example 10

The phospholipid does not dissolve in the mixture of vitamin and co-solvent even if alcohol is added.

Example 11

The mixture of vitamin, essential oil and co-solvent dissolves in alcohol. The solution after aqueous phase inversion forms an emulsion of fine distribution (the average particle size is 1.2 [μm]), which becomes somewhat rougher (the particle size increases from 1.2 [μm] to 7 [μm]) under ultrasonic treatment.

Example 12

The alcoholic dispersion of essential oil, vitamin, co-solvent and phospholipid has gel structure and contains some rough multilaminar liposomes (the average particle size is 141.5 [μm]). Under ultrasonic treatment the dispersion forms a finer mixed phase (the average particle size decreases to 41.1 [μm]).

After aqueous phase inversion a mixture forms containing mixed phase oil emulsion-liposomal gel disperse phase (average particle size is 4.7 [μm]). The ultrasonic treatment gives rise to the agglomeration of the dispersed phase (about the average size from 5.8 [μm] to 6 [μm]).

Example 13

Reference

The components and the way of their mixing is identical with those given in Example 6 with the exception that the solution containing essential oil, vitamin, co-solvent, and phospholipid is mixed with water t=20° C. (Component E). Thus a rough heterodisperse phase of amorphous gel structure forms, in which no liposome can be recognized by means of microscope. After ultrasonic treatment the rough parts become significantly smaller (from the average size of 409.8 [μm] to 28.4 [μm]), but liposome does not form. After phase inversion elicited by alcohol the average particle size of the dispersion becomes smaller (from 409.8 [μm] to 112.3 [μm]), but the dispersed phase still does not show liposome structure. Similar result is obtained after ultrasonic treatment (the average particle size decreases from 112.3 [μm] to 13.5 [μm]), but liposome does not form here either, only the dispersion disintegrates.

TABLE 2

Figure 1:
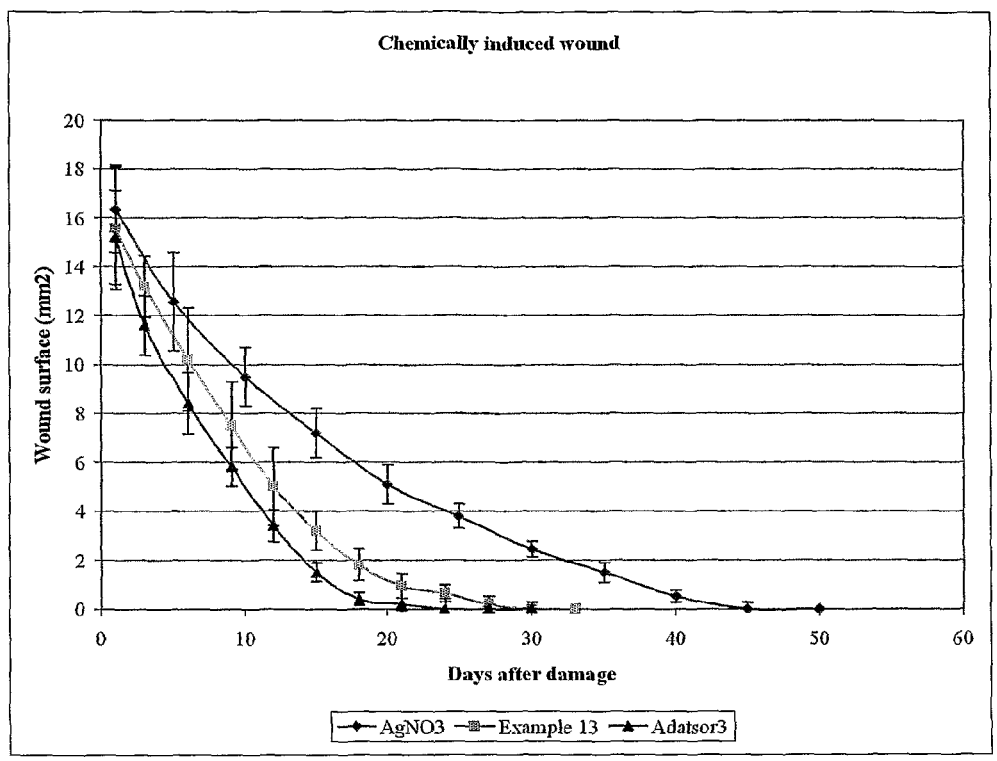
FIG. 1: Recovery after chemically induced wound.
Figure 2:
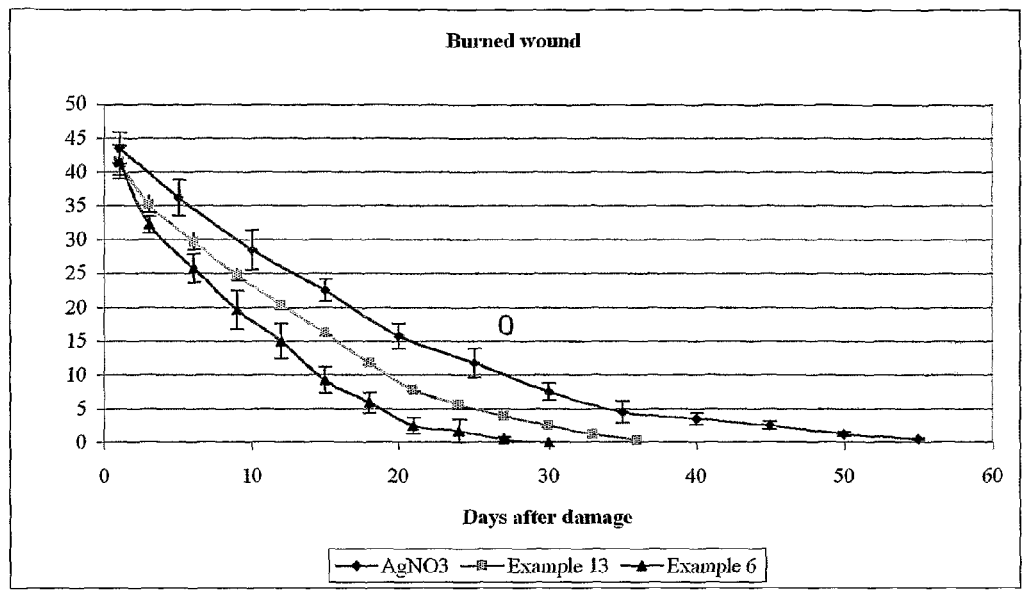
FIG. 2: Time frame of wound recovery.
Figure 3:
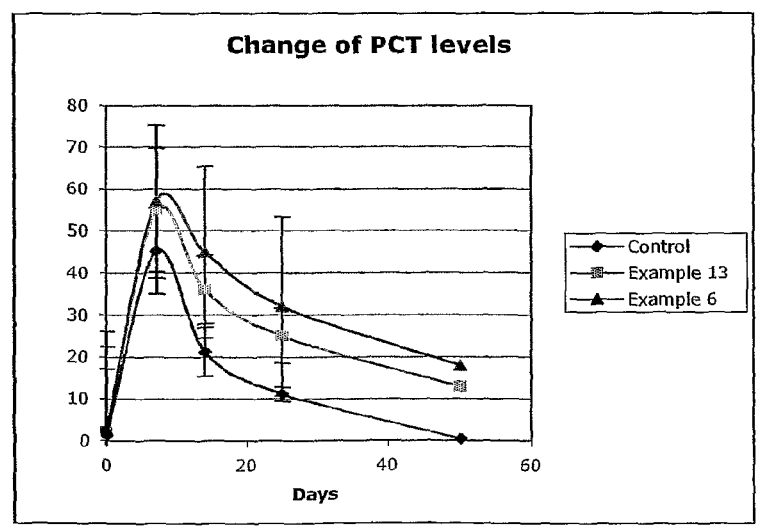
FIGS. 3 and 4: Displays results of procalcitonin and C reactive protein levels.
Figure 4:
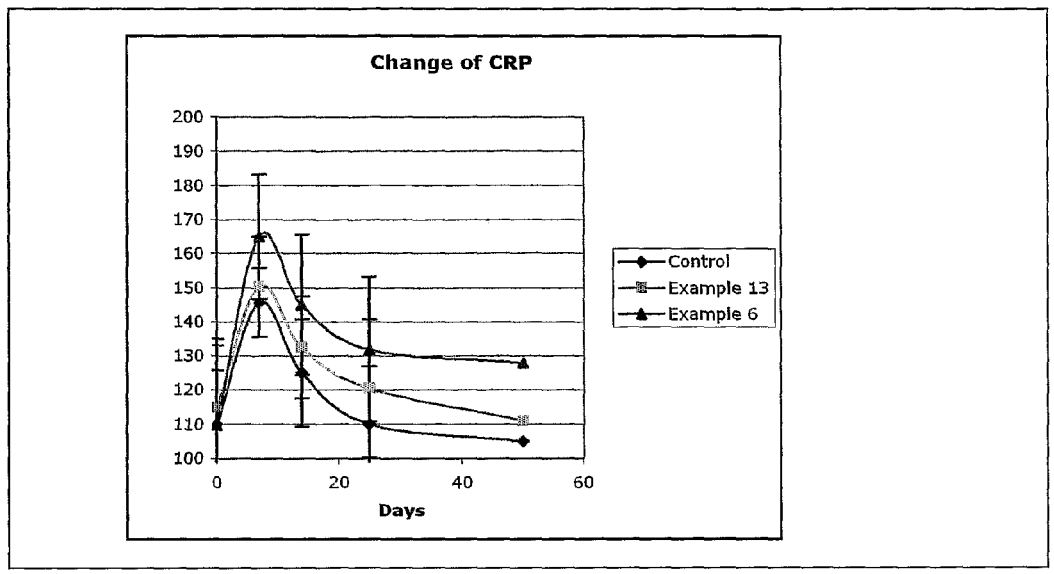
Figure 5:
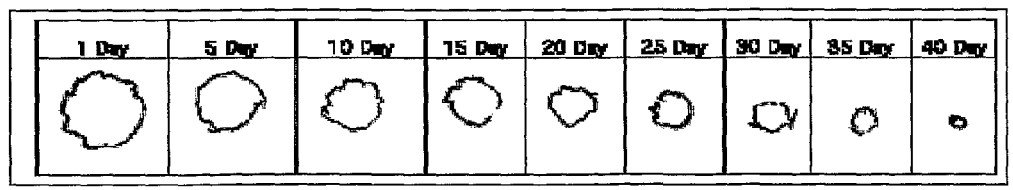
FIG. 5: Shows typical figures of the recovery of diabetic ulcers.
Figure 6:
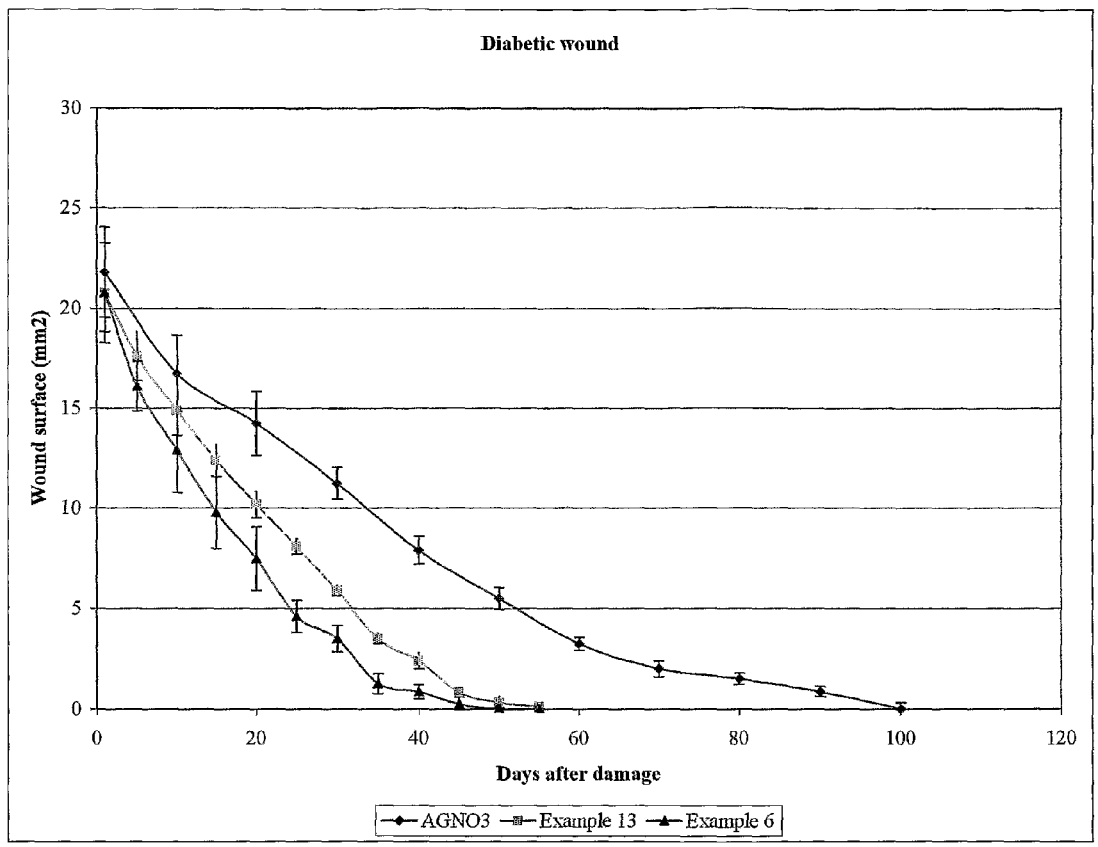
FIG. 6: Shows the time frame of the healing of the diabetic wounds.

| Components | Examples | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| A (essential oil) | + | + | − | − | + | + | + | + | − | − | + | + | + |
| B (vitamin) | − | − | + | + | + | + | − | − | + | + | + | + | + |
| D (phospholipid) | − | + | − | + | − | + | − | + | − | + | − | + | + |
| C (co-solvent) | + | + | + | + | + | + | + | + | + | + | + | + | + |
| E (water) | + | + | + | + | + | + | − | − | − | − | − | − | − |
| G (alcohol) | − | − | − | − | − | − | + | + | + | + | + | + | + |
| First series of evaluation | ⊕ | N | ⊕ | N | ⊕ | ⊕ | ON | N | ON | N | ⊕ | ⊕ | ⊕ |
| F (alcohol) | + | + | + | + | + | + | − | − | − | − | − | − | − |
| H (water) | − | − | − | − | − | − | + | + | + | + | + | + | + |
| Second series of evaluation | ON | N | ⊕ | N | ⊕ | ⊕ | ON | N | ⊕ | N | ⊕ | ⊕ | ⊕ |
| Phase inversion | hydrophilic-lipophilic | | | | | | lipophilic-hydrophilic | | | | | | hydrophilic-lipophilic |

Signs:
⊕: it can be evaluated
N: it cannot be evaluated (the phospholipid does not dissolve)
ON: solution, thus it cannot be evaluated

TABLE 3

Hydrophilic-lipophilic phase inversion
(summary of the laser particle size analysis)

| | Examples | | | | |
|---|---|---|---|---|---|
| | 1 | 3 | 5 | 6 | 13 |
| First series of evaluation (hydrophilic) | d̄ (dmax) (V %) | d̄ (dmax) (V %) | d̄ (dmax) (V %) | d̄ (dmax) (V %) | d̄ (dmax) (V %) |
| UN | 305.7 (0.4; 90; 200) (1.5; 1.5; 3.5; 4.7) | 27.3 (0.9; 6; 110) (2.2; 5.8; 1.5) | 3.6 (0.6; 4) (3.2; 8) | 478 ( (15; 600) (1.5; 7.5) | 409.8 (7; 110; 1000) (1.5; 2.5; 4.7) |
| U1P | 259.5 (0.5; 3; 700) (13.1; 1.7; 2.2; 4.4) | 7.4 (10.9; 6) (3; 8) | 6.9 (0.6; 4) (2.8; 7.4') | 68.2 (40) (5.0; 7.0) | 26 (40) (5.8) |
| U2P | 86 (0.7; 2.5; 70; 380) (1.7; 2.7; 2.0; 0.35) | 5.9 (1.6; 3; 8) | 6.6 (0.5; 4) (2.8; 7.4) | 50.1 ( (30) (60) | 284 (20) (5,8) |
| U N d (10, 50, 90) % | (0.7; 86.6; 953.6') | (0.9; 7.6; 85.1) | (0.6; 3; 7.4) | (16.7; 425; 1031.8) | (8.6; 158.7; 1112) |
| Second series of evaluation (lipophilic) | — | d̄ (dmax) (V %) | d̄ (dmax) (V %) | d̄ (dmax) (V %) | d̄ (dmax) (V %) |
| UN | — | 11.2 (0.6; 8) (3.2; 7.8) | 1.3 (0.6; 6) (10.8; 1.5) | 3.6 (1.2) (17) | 112.3 (0.4; 4; 20; 100) (5.2; 0.6; 0.8; 2) |
| U1P | — | 7.6 ( (0.6; 6) (2.8; 7.5) | 8.1 (10.8; 5; 70) (9; 1; 1.2) | 7.1 (12) (11.8) | 17.1 (0.35; 2.5; 30) (6.2; 1.3; 3.2) |
| U2P | — | 6.5 (0.6; 6) (2.8; 7.5) | 8.2 (0.8; 5; 70) (9; 1; 1.2) | 7.7 (1.5) (116) | 13 (0.45; 3.5; 3) (6.2; 1.5; 3.2) |
| U N d (10, 50, 90) % | — | (0.5; 5.5; 28.5) | (0.4; 0.8; 2.1) | (0.9; 1.4; 2.4) | (0.4; 9.2; 376.8) |

TABLE 4

Lipophilic-hydrophilic phase inversion (summary of the laser particle size analysis)

| | Examples | | |
|---|---|---|---|
| | 9 d̄ (dmax)(V %) | 11 d̄ (dmax)(V %) | 12 d̄ (dmax)(V %) |
| First evaluation series (lipophilic) | | | |
| UN | — | — | 141.5(0.3; 3; 80; 1000)(0.8; 1; 4.2; 1) |
| U1P | — | — | 50.8(0.3; 3; 30; 300)(0.7; 1.5; 5.2; 0.7) |
| U2P | — | — | 41.1;(0.5; 6)(0.8; 6) |
| U N d (10, 50, 90) % | — | — | (2.3; 45.7; 341.8) |
| Second evaluation series (hydrophilic) | | | |
| UN | 0.6(0.4)(9.2) | 1.2(1.2)(25) | 4.7(1.4; 40)(7.8; 0.8) |
| U1P | 3.4(0.4; 5.0; 50)(8; 0.5; 0.5) | 6.8(1.2; 9; 50)(21; 0.5; 1) | 5.8(2; 45)(7.8; 1') |
| U2P | 2.9(0.4; 9; 50)(8; 0.8; 2.5) | 7.0(1.2; 9; 50)(21; 0.5; 1) | 6.0(2.45)(6.8) |
| U N d (10, 50, 90) % | (0.3; 0.5; 1.2) | (0.9; 1.2; 1.7) | (0.9; 2.2; 9.7) |

The invention claimed is:

1. A liposome composition consisting essentially of: 0.5-5.0 parts by weight of a pharmaceutical grade citrus essential oil, 0.5-5.0 parts by weight of a pharmaceutical grade lavender oil, 0.1-1.5 parts by weight of vitamin E, 0.1-1.5 parts by weight of vitamin A, 1.0-6.0 parts by weight of ethoxylated castor oil, 0.1-1.0 parts by weight of a phospholipid, 15-30 parts by weight of distilled water, and 65-75 parts by weight of 96% ethanol; wherein said composition is for treating a wounded skin surface, a burned skin surface, a frozen skin surface, an inflamed skin surface, eczema, stretch marks, cellulitis or an infected skin surface and wherein all of said parts by weight are parts by weight of the liposome composition.

2. The composition according to claim 1, wherein the citrus essential oil is present at 1.5 parts by weight.

3. The composition according to claim 1, wherein the lavender oil is present at 2.0 parts by weight.

4. The composition according to claim 1, wherein the vitamin E is present at 0.5 parts by weight.

5. The composition according to claim 1, wherein the vitamin A is present at 3.5 parts by weight.

6. The composition according to claim 1, wherein the phospholipid is present at 0.5 parts by weight.

7. The composition according to claim 1, wherein the ethoxylated castor oil is present at 3.5 parts by weight.

8. The composition according to claim 1, wherein the distilled water is present at 23 parts by weight.

9. The composition according to claim 1, wherein the ethyl alcohol is present at 68 parts by weight.

10. The composition according to claim 1, wherein the citrus essential oil is a lemon oil.

11. The composition according to claim 1, wherein the phospholipid is soy lecithin.

12. The composition according to claim 1, wherein ethylene oxide is present in the ethoxylated castor oil at a concentration of 30-40 mol.

13. The composition according to claim 1, wherein ethylene oxide is present in the ethoxylated castor oil at a concentration of 35 mol.

14. The composition according to claim 1, wherein the citrus essential oil is from an Aurantioidea plant.

15. A process for the preparation of the liposomal composition according to claim 1 comprising:
(a) mixing 0.5-5.0 parts by weight of the citrus essential oil and 0.5-5.0 parts by weight of the lavender oil to form mixture 1;
(b) mixing 0.1-1.0 parts by weight of vitamin E and 0.1-1.5 parts by weight of vitamin A to form mixture 2,
(c) adding mixture 1 and mixture 2 to form mixture 3;
(d) adding 1.0-6.0 parts by weight of ethoxylated castor oil to mixture 3 and dissolving 0.1-1.0 parts by weight of phospholipid in an oil phase obtained after the addition of the ethoxylated castor oil to form mixture 4; and carrying out either:
(e) adding 15-30 parts by weight of distilled water at 45° C. to mixture 4, thereby forming a liposomal hydrophilic phase and adding 65-75 parts by weight of 96% ethanol, wherein the addition of said ethanol to the liposomal hydrophilic phase elicits a conversion of the liposomal hydrophilic phase into a liposomal lipophilic composition by phase inversion;
or
(f) adding 65-75 parts by weight of 96% ethanol to mixture 4, thereby forming a liposomal lipophilic phase and adding 15-30 parts by weight of distilled water at 45° C., wherein the addition of said distilled water to the liposomal lipophilic phase elicits a conversion of the liposomal lipophilic phase into a liposomal hydrophilic composition by phase inversion; wherein said parts by weight are parts by weight of the liposomal composition.

16. The process according to claim 15, wherein step (e) is carried out.

17. A method for treating skin damage comprising contacting a damaged skin with the composition according to claim 1, wherein the damaged skin is selected from at least one of: a wounded skin surface, a burned skin surface, a frozen skin surface, an inflamed skin surface, eczema, stretch marks, cellulitis and an infected skin surface.

18. The method of claim 17, wherein the damaged skin is a wounded skin surface and wherein the wounded skin surface is a chemically initiated wound or a diabetic wound.

19. The method of claim 17, wherein the damaged skin is an infected skin surface, and wherein said infected skin surface is foot mycosis.

* * * * *